US008845921B2

(12) United States Patent
Merkel et al.

(10) Patent No.: US 8,845,921 B2
(45) Date of Patent: *Sep. 30, 2014

(54) SEPARATION OF CLOSE BOILING COMPOUNDS BY ADDITION OF A THIRD COMPOUND

(75) Inventors: Daniel C. Merkel, Orchard Park, NY (US); Konstantin A. Pokrovski, Orchard Park, NY (US); Hsueh S. Tung, Getzville, NY (US); Hang T. Pham, Amherst, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 793 days.

This patent is subject to a terminal disclaimer.

(21) Appl. No.: 12/749,207

(22) Filed: Mar. 29, 2010

(65) Prior Publication Data

US 2010/0187088 A1 Jul. 29, 2010

Related U.S. Application Data

(63) Continuation-in-part of application No. 12/406,653, filed on Mar. 18, 2009, now Pat. No. 8,034,251.

(60) Provisional application No. 61/043,451, filed on Apr. 9, 2008.

(51) Int. Cl.
*C09K 5/04* (2006.01)
*C07C 17/386* (2006.01)
*B01D 3/36* (2006.01)

(52) U.S. Cl.
CPC ............... *B01D 3/36* (2013.01); *C07C 17/386* (2013.01)
USPC ............. 252/67; 510/177; 510/410; 510/408; 570/155; 570/177

(58) Field of Classification Search
USPC ............. 252/67; 510/177, 410, 408; 570/155, 570/177
See application file for complete search history.

(56) References Cited

U.S. PATENT DOCUMENTS

| | | | | |
|---|---|---|---|---|
| 4,944,846 A | * | 7/1990 | Manzer et al. | 203/1 |
| 5,211,817 A | * | 5/1993 | Adams et al. | 203/82 |
| 6,060,629 A | * | 5/2000 | Pham et al. | 570/178 |
| 8,034,251 B2 | * | 10/2011 | Merkel et al. | 252/67 |
| 8,058,486 B2 | * | 11/2011 | Merkel et al. | 570/155 |
| 8,070,975 B2 | * | 12/2011 | Pham et al. | 252/67 |
| 8,084,653 B2 | * | 12/2011 | Tung et al. | 570/123 |
| 8,114,308 B2 | * | 2/2012 | Merkel et al. | 252/67 |
| 8,158,836 B2 | * | 4/2012 | Pigamo et al. | 570/153 |
| 8,168,837 B2 | * | 5/2012 | Merkel et al. | 570/177 |
| 2002/0142927 A1 | | 10/2002 | Pham et al. | |
| 2006/0030508 A1 | | 2/2006 | Pham et al. | |
| 2006/0106263 A1 | * | 5/2006 | Miller et al. | 570/155 |
| 2007/0007488 A1 | | 1/2007 | Singh et al. | |
| 2007/0197842 A1 | | 8/2007 | Mukhopadhyay et al. | |
| 2008/0045758 A1 | | 2/2008 | Cohn et al. | |
| 2009/0240090 A1 | * | 9/2009 | Merkel et al. | 570/160 |
| 2009/0242832 A1 | * | 10/2009 | Pham et al. | 252/182.12 |
| 2010/0048961 A1 | * | 2/2010 | Merkel et al. | 570/160 |
| 2010/0187088 A1 | | 7/2010 | Merkel et al. | |
| 2012/0037843 A1 | * | 2/2012 | Pham et al. | 252/79.3 |
| 2012/0065437 A1 | * | 3/2012 | Merkel et al. | 570/175 |

FOREIGN PATENT DOCUMENTS

| | | |
|---|---|---|
| EP | 0472391 B1 | 1/1996 |
| WO | WO2007079431 A2 | 7/2007 |
| WO | WO2008054781 A1 | 5/2008 |
| WO | WO2009003084 A1 | 12/2008 |
| WO | WO2009009421 A1 | 1/2009 |

OTHER PUBLICATIONS

CIPO Search Report dated Nov. 5, 2012 and First Office Action, CN Appl. 200910203979.1, filed Apr. 8, 2009. CN.
Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

* cited by examiner

*Primary Examiner* — Douglas McGinty
(74) *Attorney, Agent, or Firm* — Bruce O. Bradford

(57) ABSTRACT

The invention provides a method for separating halocarbons. In particular, a method for separating 2-chloro-1,1,1,2-tetrafluoropropane (HCFC-244bb) from 2-chloro-3,3,3-trifluoropropene (HCFC-1233xf) by adding a third component and then separating via conventional distillation. More particularly the invention pertains to a method for separating HCFC-244bb from HCFC-1233xf which are useful as intermediates in the production of 2,3,3,3-tetrafluoropropene (HFO-1234yf).

11 Claims, No Drawings

US 8,845,921 B2

SEPARATION OF CLOSE BOILING COMPOUNDS BY ADDITION OF A THIRD COMPOUND

CROSS REFERENCE TO RELATED APPLICATIONS

This application is a continuation-in-part of U.S. application Ser. No. 12/406,653 filed on Mar. 18, 2009 (now U.S. Pat. No. 8,034,251) which claimed the benefit of U.S. Provisional Application No. 61/043,451 filed on Apr. 9, 2008, the contents of which are incorporated herein by reference.

FIELD OF THE INVENTION

The present invention provides a method for separating halocarbons in an azeotropic composition.

BACKGROUND OF THE INVENTION

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials, it is desirable to use fluids having the lowest possible greenhouse warming potential in addition to zero ozone depletion potential. Thus, there is considerable interest in developing environmentally friendlier materials for the applications mentioned above.

Tetrafluoropropenes, having zero ozone depletion and low global warming potential, have been identified as potentially filling this need. While the toxicity, boiling point, and other physical properties in this class of chemicals vary greatly from isomer to isomer, one tetrafluoropropene having valuable properties is 2,3,3,3-tetrafluoropropene (HFO-1234yf). HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

During one process of producing HFO-1234yf, 2-chloro-3,3,3-trifluoropropene (HCFO-1233xf) and 2-chloro-1,1,1,2-tetrafluoropropane (HCFC-244bb) are produced as a first and second intermediate compounds, respectively. Specifically, HFO-1234yf is made from a 3 reaction step process. The first step is the reaction of pentachloropropane or tetrachloropropene with HF to form HCFO-1233xf. The second step is the hydrofluorination of HCFO-1233xf with HF to form HCFC-244bb, and the third step is the dehydrochlorination reaction of HCFC-244bb to form HFO-1234yf. Incomplete reaction in the second step reaction will result in a stream containing both HCFC-244bb and HCFO-1233xf. Such a reaction is well known in the art and is described in U.S. Applications 20070007488, 20070197842, and 20090240090, the specifications of which are incorporated herein by reference.

One problem with this process is that HCFC-244bb and HCFO-1233xf are inseparable using conventional separation techniques known in the art because together they form a binary azeotrope or azeotrope-like composition, which is described in U.S. Patent Application 20090242832, the specification of which is incorporated herein by reference. If, after reaction, there remains a relatively large amount of unreacted HCFO-1233xf in the resulting crude organic material this would require most of, if not all of, the stream to be recycled back to the reactor for additional conversion before proceeding to the next reaction step. This would be very costly from a capital (equipment size) requirement and a manufacturing standpoint. In addition, the presence of appreciable amounts of olefins, such as HCFO-1233xf, in the HCFC-244bb feed material to the next step of the 2,3,3,3-tetrafluoropropene manufacturing process may be detrimental to the dehydrochlorination catalyst.

Previously, various methods of separating azeotropic mixtures of fluorocarbons have been suggested. European patent application EP 0 472 391, for example, suggests separating HFC-134a from a mixture containing hydrochlorofluorocarbons using an extraction agent such as trichloroethylene or perchloroethylene, among others. U.S. Pat. No. 5,211,817 also attempts a separation of fluorocarbons from azeotropic mixtures with HF by column distillation and withdrawing a vapor sidestream followed by introducing the sidestream into a rectifying column equipped with a condenser and operated at a high reflux ratio. These proposals, however, provide less than satisfactory solutions to the instant problem. Thus, there is a need for a new manufacturing process for the production of tetrafluoropropenes and in particular 2,3,3,3-tetrafluoropropene.

SUMMARY OF THE INVENTION

The present invention relates to a method for separating a first halocarbon from a second halocarbon, which are binary azeotropes in solution. More specifically, a third component is added to the binary azeotropic mixture such that the third component forms a ternary azeotrope with the first halocarbon and the second halocarbon in solution wherein the ternary azeotrope is a stronger azeotrope than the binary azeotrope. The ternary azeotrope is then distilled from the solution such that at least portion of the first halocarbon remains and substantially all of the second halocarbon is removed. In one embodiment, the first and second halocarbons may be intermediates in the production of a tetrafluoropropene, such as 2,3,3,3-tetrafluoropropene. In even further embodiments, the first and second halocarbons are HCFC-244bb and HCFO-1233xf, respectively, and the third component hydrogen fluoride.

The resulting ternary azeotrope may have a concentration of the first halocarbon between about 10.0-18.0 wt %. The concentration of the second halocarbon in the ternary azeotrope may be between about 51.0-64.0 wt %, and the concentration of the third component in the ternary azeotrope may be between about 23-35 wt %.

The boiling point of the ternary azeotrope may be about 0° C. to about 61° C. at a pressure of about 15 psia to about 108 psia. To this end, in one embodiment the boiling point may be about 23° C. at a pressure of about 37 psia, about 0° C. at a pressure of about 15 psia, or about 61° C. at a pressure of about 108 psia.

A further aspect of the instant invention includes a method for separating HCFC-244bb from a binary azeotropic mixture with HCFO-1233xf by first adding a hydrogen fluoride to the binary azeotropic mixture such that HCFC-244bb, HCFO-1233xf, and hydrogen fluoride form a ternary azeotropic mixture The resulting ternary azeotrope is then distilled from the solution such that a portion of HCFC-244bb remains in solution and substantially all of the HCFO-1233xf is removed. In certain embodiments, approximately 60 to 97% of HCFC-244b is recovered.

In certain embodiments of the foregoing, approximately 10 to 50 wt % of the binary mixture is comprised of the HCFC- 244bb and approximately 50 to 90 wt % of the binary mixture is comprised of HCFO-1233xf. When approximately 0.1-10 wt % of hydrogen fluoride is added to the binary mixture to form the ternary azeotropic mixture, the resulting ternary azetropic mixture has a concentration of about 10.0-18.0 wt % of HCFC-244bb; about 51.0-64.0 wt % of HCFO-1233xf, and the concentration of hydrogen fluoride is about 23-35 wt %.

The boiling point of the ternary azetrope may be about 0° C. to about 61° C. at a pressure of about 15 psia to about 108 psia. To this end, in one embodiment the boiling point may be about 23° C. at a pressure of about 37 psia, about 0° C. at a pressure of about 15 psia, or about 61° C. at a pressure of about 108 psia.

Additional embodiments and advantages in the instant invention will be readily apparent to one of ordinary skill in the art based on the disclosure provided herein.

DETAILED DESCRIPTION OF THE INVENTION

The instant provides, at least in part, a novel methodology for separating HCFC-244bb from a composition of HCFC-244bb and HCFO-1233xf by adding a third, non-halocarbon component, namely hydrogen fluoride. Such a mixture forms a ternary azeotrope or azeotrope-like composition with HCFC-244bb and HCFO-1233xf, which requires less HCFC-244bb relative to HCFO-1233xf than the binary HCFC-244bb/HCFO-1234xf azeotrope or azeotrope-like composition. It was surprisingly discovered that HCFO-1233xf and HCFC-244bb form a relatively weak azeotrope compared to that of the ternary azeotrope-like composition of 1233xf/244bb/HF. This allows for a much more effective separation of 244bb from 1233xf using realistic sized and commercially feasible conventional fractional distillation equipment.

As noted above, in the process of manufacturing HFO-1234yf, one commences with a mixture of a first halocarbon (e.g. HCFO-1233xf) and a second halocarbon (e.g. HCFC-244bb), which form an azeotropes or azeotrope-like composition. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. Accordingly, as used herein, an azeotrope is a liquid mixture that exhibits a maximum or minimum boiling point relative to the boiling points of surrounding mixture compositions. For the purpose of this invention, an "azeotrope-like" composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation.

One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance.

Another characteristic of azeotrope-like compositions is that there is a range of compositions containing the same components in varying proportions which are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

The instant invention presents, at least in part, a method of isolating 244bb from its azeotropic relationship with HCFO-1233xf by adding an effective amount of anhydrous hydrogen fluoride. More specifically, the mixture of 2-chloro-1,1,1,2-tetrafluoropropane (244bb) and 2-chloro-3,3,3-trifluoropropene (1233xf) is added to a conventional fractional distillation column and the distillation column operated by either batch or continuous mode. In one embodiment, the organic portion of the azeotropic or azeotrope-like composition is a mixture of HCFC-244bb/HCFO-1233xf containing from about 50 to about 90 weight percent HCFO-1233xf, preferably from about 51.5 weight percent to about 86.5 weight percent and more preferably from about 53 weight percent to about 83 weight percent based on the weight of the organic portion of the azeotropic or azeotrope-like composition. In further embodiments, the organic portion of the azeotropic or azeotrope-like composition is a mixture of HCFC-244bb/HCFO-1233xf, containing from about 10 to about 50 weight percent HCFC-244bb, preferably from about 13.5 weight percent to about 48.5 weight percent and more preferably from about 17 weight percent to about 47 weight percent based on the weight of the organic portion of the azeotropic or azeotrope-like composition. A relatively small amount of anhydrous hydrogen fluoride, typically between 0.1-10 wt %, is then added to the said distillation column as a third component forming a ternary azeotropic mixture.

The resulting ternary azeotrope has a concentration of 244bb between about 10.0-18.0 wt % depending on the pressure; a concentration of 1233xf between about 51.0-64.0 wt % depending on the pressure; and a concentration of HF between about 23-35 wt % depending on the pressure.

The ternary azeotrope has a boiling point of about from 0° C. to about 61° C. at a pressure of about 15 psia to about 108 psia. In one embodiment it has a boiling point of about 23° C. at a pressure of about 37 psia. In another embodiment it has a boiling point of about 0° C. at a pressure of about 15 psia. In another embodiment it has a boiling point of about 61° C. at a pressure of about 108 psia.

The foregoing wt percentages and boiling points are based, at least in part, on the surprising discovery that the ternary azeotrope-like composition of 1233xf/244bb/HF is much stronger than that of the binary HCFO-1233xf/HCFC-244bb azeotrope. Strength of the azeotrope may be measured based upon a comparison of vapor pressure measurements of the mixtures, as can be seen, for example, in Tables 1 and 2 below. Table 1 is the Vapor pressure measurement for the 1233xf/244bb binary mixture. The vapor pressures of pure HCFO-1233xf, HCFC-244bb and 50/50% mixture of HCFO-1233xf/HCFC-244bb were measured. The results in Table 1 below show that the vapor pressure of this mixture is higher than the vapor pressure of either pure component HCFO-1233xf, and HCFC-244bb at 0, 25 and 60° C. Note however the small vapor pressure difference between the pure components and the 50/50 mixture. This indicates a relatively weak interaction or relatively weak azeotrope or azeotrope-like binary composition. On the other hand, the results in Table 2 below show a P-x-y diagram for the ternary compositions containing a mixture of 2-chloro-3,3,3-trifluoropropene (HCFO-1233xf) and 2-chloro-1,1,1,2-tetrafluoropropane (HCFC-244bb) (50/50%) and HF. They were blended to form a ternary heterogeneous azeotrope mixtures at different compositions. The vapor pressures of the mixtures were measured at about 0, 25 and 61° C. and the following results were noticed. Table 2 shows the vapor pressure measurements of HCFO-1233xf, HCFC-244bb, and HF as a function of composition with varying weight percent HF at constant temperatures of about 0° C., 25° C., and 61° C. The data also showed that in this range of hydrogen fluoride concentration the mixture of HCFO-1233xf/HCFC-244bb/HF is heterogeneous and that the vapor pressure of this mixture is significantly higher than the vapor pressure of either pure component HCFO-1233xf, and HCFC-244bb at 0, 25 and 60° C. The significant vapor pressure difference between the pure components and the 244bb/1233xf/HF ternary mixtures indicates a relatively strong interaction or relatively strong azeotrope or azeotrope-like composition as compared to the 1233xf/244bb binary azeotrope or azeotrope-like composition.

TABLE 1

Vapor Pressure of HCFO-1233xf/HCFC-244bb mixture

| T (° C.) | Pressure (Psia) | Wt. % HCFO-1233xf/ HCFC-244bb |
|---|---|---|
| 0.0 | 8.87 | 100.0/0.0 |
|  | 9.43 | 50.0/50.0 |
|  | 8.24 | 0.0/100.0 |
| 25.0 | 22.88 | 100.0/0.0 |
|  | 23.81 | 50.0/50.0 |
|  | 21.33 | 0.0/100.0 |
| 60.0 | 64.58 | 100.0/0.0 |
|  | 64.98 | 50.0/50.0 |
|  | 59.75 | 0.0/100.0 |

TABLE 2

P-T-X of [HCFO-1233xf/HCFC-244bb (50/50%)]/HF

|  | Pressure (Psia) | | |
|---|---|---|---|
| Wt. % HF | T = 0° C. | T = 25° C. | T = 61° C. |
| 0 | 9.4 | 23.8 | 65.0 |
| 7.29 | 15.2 | 38.4 | 104.0 |
| 14.59 | 15.2 | 38.5 | 107.7 |
| 22.13 | 15.1 | 38.4 | 107.2 |
| 31.60 | 15.1 | 38.3 | 107.2 |
| 37.32 | 15.1 | 38.5 | 107.2 |
| 100.0 | 6.87 | 17.8 | 52.4 |

Based on this characterization, the distillation column containing the ternary azeotrope is brought to total reflux and ternary azeotrope or azeotrope-like composition of 1233xf/244bb/HF is concentrated at the top of the column, thus, separating the ternary azeotrope from the remaining 244bb. Distillate is then continuously removed from the top of the distillation column and additional HF is added continuously to the distillation column to make up for what has been removed as distillate. This will ensure a relatively constant distillate composition. If the distillation is run in batch mode make-up HF feed is continued until the desired purity of HCFC-244bb is achieved in the reboiler. If the distillation is run in continuous mode make-up HF and 1233xf/244bb mixture in the correct proportions are fed continuously to maintain desired purity of HCFC-244bb in the continuous distillation bottoms stream. Because the ternary azeotrope forms such a strong interaction, required separation of 244bb from 1233xf is able to be achieved using more realistically sized and commercially feasible conventional fractional distillation equipment than would be required when separation is performed without HF present.

The source of the HF can either be external or from the 1233xf hydrofluorination reaction (to make 244bb). The stream exiting the 1233xf hydrofluorination reactor may have to be treated to adjust the HF concentration before being fed forward to the 1233xf/244bb distillation column. Other impurities exiting the 1233xf hydrofluorination reactor with 1233xf and 244bb may be separated prior to or after the 1233xf/244bb distillation column.

The following non-limiting examples serve to illustrate the invention.

Example 1

An ebulliometer comprising a vacuum jacketed tube with a condenser on top which is further equipped with a Quartz Thermometer was used. About 20.91 g HCFO-1233xf was charged to the ebulliometer and then HCFC-244bb was added in small, measured increments. Temperature depression was observed when HCFC-244bb is added to HCFO-1233xf, indicating a binary minimum boiling azeotrope was formed. From greater than about 0 to about 5 weight percent 244bb, the boiling point of the composition stays below or around the boiling point of 1233xf. The boiling temperature of HCFO-1233xf (99.99% pure) was about 12° C. at 14.5 psia. The boiling point of HCFC-244bb was about 14.0 at 14.5 psia. The binary mixtures shown in Table 1 were studied. The compositions exhibit azeotrope and/or azeotrope-like properties over this range.

TABLE 1

HCFO-1233xf/HCFC-244bb Compositions at P = 14.4 psia.

| T (° C.) | Wt. % HCFO-1233xf | Wt. % HCFC-244bb |
|---|---|---|
| 9.79 | 98.35 | 1.65 |
| 9.78 | 96.54 | 3.46 |
| 9.78 | 94.83 | 5.17 |
| 9.85 | 93.18 | 6.82 |
| 9.95 | 91.11 | 8.89 |
| 10.00 | 87.45 | 12.45 |
| 10.25 | 83.91 | 16.09 |
| 10.36 | 80.86 | 19.14 |
| 10.43 | 76.37 | 23.63 |

Example 2

The vapor pressure of pure HCFO-1233xf, HCFC-244bb and 50/50% mixture of HCFO-1233xf/HCFC-244bb was measured. The result in Table 2 shows that the vapor pressure of this mixture is higher than the vapor pressure of either pure component HCFO-1233xf, and HCFC-244bb at 0, 25 and 60° C.

TABLE 2

Vapor Pressure of HCFO-1233xf/HCFC-244bb mixture

| T (° C.) | Pressure (Psia) | Wt. % HCFO-1233xf/ HCFC-244bb |
|---|---|---|
| 0.0 | 8.87 | 100.0/0.0 |
|  | 9.43 | 50.0/50.0 |
|  | 8.24 | 0.0/100.0 |

TABLE 2-continued

Vapor Pressure of HCFO-1233xf/HCFC-244bb mixture

| T (° C.) | Pressure (Psia) | Wt. % HCFO-1233xf/HCFC-244bb |
|---|---|---|
| 25.0 | 22.88 | 100.0/0.0 |
| | 23.81 | 50.0/50.0 |
| | 21.33 | 0.0/100.0 |
| 60.0 | 64.58 | 100.0/0.0 |
| | 64.98 | 50.0/50.0 |
| | 59.75 | 0.0/100.0 |

Example 3

29.4 lbs of a mixture of 244bb and 1233xf were charged to the same distillation apparatus as described in Example 3. The composition of the mixture was about 45.6 GC area % 244bb and 54.4 GC area % 1233xf. The distillation column was brought to total reflux at an operating pressure of 25 psig and a d/p of 8-10" $H_2O$. The composition of the overhead was analyzed several times by GC and showed a range of 30-33 GC area % 244bb and 67-70 GC area % 1233xf. Distillate was then continuously taken off the top of the column/condenser to a collection cylinder at 0.25-0.5 lb/hr.

Pressure was increased on the still to about 100 psig to see if the overhead concentrations (separation) of 244bb and 1233xf would change. The increase in pressure did not appear to have any effect on the O/H concentrations.

As distillate take-off continued, the 244bb concentration in the distillate samples continued to increase as expected. Reboiler samples started to be taken at regular intervals to monitor the progress of the distillation. As expected the concentration of 244bb in the reboiler continued to increase as the distillation progressed.

The highest purity level achieved in the reboiler samples was 98.1 GC area %. After the column was cooled down and the reboiler was drained, only a total of 667 grams of 93 GC area % 244bb was recovered.

Example 4

After the distillation results of Example 3 were obtained, the separation of 244bb and 1233xf was attempted in a distillation column having 75 theoretical stages. A 49 GC area % 244bb/51 GC area % 1233xf mixture were charged to the batch distillation column and carefully distilled at a pressure of about 20 psig. Results from the GC analysis of overhead and reboiler samples as the distillation progressed were very similar to those of Example 3.

The conclusion drawn was that 244bb and 1233xf cannot be separated by a reasonably sized conventional fractionation distillation column.

Example 5

Ternary compositions containing a mixture of 2-chloro-3,3,3-trifluoropropene (HCFO-1233xf) and 2-chloro-1,1,1,2-tetrafluoropropane (HCFC-244bb) (50/50%) and HF were blended to form a ternary heterogeneous azeotrope mixtures at different compositions. The vapor pressures of the mixtures were measured at about 0, 25 and 61° C. and the following results were noticed. Table 1 shows the vapor pressure measurements of HCFO-1233xf, HCFC-244bb, and HF as a function of composition with varying weight percent HF at constant temperatures of about 0° C., 25° C., and 61° C. The data also showed that in this range of hydrogen fluoride concentration the mixture of HCFO-1233xf/HCFC-244bb/HF is heterogeneous.

TABLE 1

P-T-X of [HCFO-1233xf/HCFC-244bb (50/50%)]/HF

| | Pressure (Psia) | | |
|---|---|---|---|
| Wt. % HF | T = 0° C. | T = 25° C. | T = 61° C. |
| 0 | 9.4 | 23.8 | 65.0 |
| 7.29 | 15.2 | 38.4 | 104.0 |
| 14.59 | 15.2 | 38.5 | 107.7 |
| 22.13 | 15.1 | 38.4 | 107.2 |
| 31.60 | 15.1 | 38.3 | 107.2 |
| 37.32 | 15.1 | 38.5 | 107.2 |
| 100.0 | 6.87 | 17.8 | 52.4 |

The data also show that the mixture is azeotropic or azeotrope-like since the vapor pressure of the ternary mixtures of HCFO-1233xf/HCFC-244bb (50/50%) and HF is higher, at all indicated blend proportions, than vapor pressures of HCFO-1233xf/HCFC-244bb (50/50%) and HF alone, i.e. as indicated in the first and last rows of Table 1 when HF is 0.0 wt. % and HCFO-1233xf/HCFC-244bb is at 100.0 wt. % as well as when HCFO-1233xf/HCFC-244bb (50/50%) is at 0.0 wt. % and HF is at 100.0 wt. %.

Example 6

The azeotropic or azeotrope-like composition of the ternary (HCFO-1233xf/HCFC-244bb)(50/50%)/HF mixture was also verified by Vapor-Liquid-Liquid equilibrium (VLLE) experiment. 13 g of HCFO-1233xf/HCFC-244bb (50/50%) were mixed with 7.8 g of HF to form a heterogeneous mixture (visual observation) at 23° C. The vapor composition was sampled. The result shows that the vapor composition is about 18±2 wt. % HF at 23° C.

Example 7

The azeotropic or azeotrope-like composition of the ternary (HCFO-1233xf/HCFC-244bb)(50/50%)/HF mixture was also verified by Vapor-Liquid-Liquid equilibrium (VLLE) experiment. 38.9 g of HCFO-1233xf/HCFC-244bb (5050%) were mixed with 37.3 g of HF to form a heterogeneous mixture (visual observation) at 23° C. The vapor composition and the organic rich layer were sampled. The result shows that the vapor composition is about 14±2 wt. % HF at 23° C., consistent with the results obtained in the other two-phase region experiment described in Example 6.

Example 8

The azeotropic or azeotrope-like composition of the ternary (HCFO-1233xf/HCFC-244bb)(50/50%)/HF mixture was also verified by Vapor-Liquid-Liquid equilibrium (VLLE) experiment. 9 g of HCFO-1233xf/HCFC-244bb (50/50%) were mixed with 15 g of HF to form a homogeneous mixture (visual observation) at 23° C. The vapor composition was sampled. The result shows that the vapor composition is about 31±2 wt. % HF at 23° C. This observation is in agreement with examples 1 and 2 for the single phase (homogeneous) region.

Example 9

37.4 pounds of the material containing 3 weight percent HF balanced with mixture of organics consisting of 44.4 weight percent HCFC-244bb and 55.6 weight percent HCFO-1233xf was charged into a batch distillation column. The mixture was homogeneous. The fractionation distillation column consisted of a 10 gallon reboiler, 2 inch ID by 8 feet column packed with ¼" Pro-Pak Metal High Efficiency Distillation Column Packing, and a shell and tube condenser. The column had about 30 theoretical plates. The distillation column was equipped with temperature, pressure, and differential pressure transmitters. The distillation was run at pressure of about 23-25 psig and a d/p of 8-10" H$_2$O. Distillate was continuously taken off the top of the column/condenser. This distillate was sampled, titrated for HF concentration determination, and analyzed by GC at regular intervals. Analysis showed a ternary azeotrope of HF/HCFC-244bb/HCFO-1233xf. The HF concentration of the azeotrope was analyzed to be about 25-33 wt % HF using titration with 0.1; N KOH. The organic concentration based on GC area % was about 17-21 GC area % HCFC-244bb and about 79-83 GC area % HCFO-1233xf. At a pressure of 23-25 psig the column overhead temperature was about 23° C. for this composition.

Example 10

The following example used a Monel distillation column consisting of a 2 liter reboiler, 1 inch ID×4 feet long helicoil packed column, and tube and shell condenser. The column was equipped with temperature, pressure, and differential pressure transmitters. 1000 grams of material containing about 3.2 wt % HF balanced with mixture of organics consisting of about 51 weight percent HCFC-244bb and 49 weight percent HCFO-1233xf were charged into the distillation system. The mixture was homogeneous. The distillation was performed at a pressure 7-29 psig. Analysis of distillate samples showed consistent results at a pressure above 18 psig. The organic composition by GC was determined to be about 21-23 GC Area % HCFC-244bb and about 79-77 GC Area % HCFO-1233xf and the concentration of HF in the distillate was found to be about 25-29 weight % HF using titration with 0.1; N NaOH. The decrease in the amount of HF in the sample occurred sharply indicating a ternary azeotrope of HCFC-244bb/HCFO-1233xf/HF.

Example 11

This example illustrates calculated 244bb recovery from the mixture of 244bb and 1233xf. The calculations are based on the results of Example 10. This example further illustrates a method for separating 244bb/1233xf via distillation in the presence of HF. The calculations of the required amount of HF and 244bb recovery are presented in the Table 3. The given calculations are based on the ternary azeotrope with a composition 22 wt % 244bb/78 wt %1233xf, organics: HF=72:28 (that was observed in Example 10) recovery via distillation of 244bb/1233xf mixture with addition of HF.

| component | Feed to the system g/hr | OH take-off g/hr | Bottoms take-off g/hr | 244bb recovery % |
|---|---|---|---|---|
| 244bb | 400 | 150 | 250 | 62.5 |
| 1233xf | 600 | 600 | 0 | |
| HF | 292 | 292 | 0 | |
| 244bb | 500 | 141 | 359 | 71.8 |
| 1233xf | 500 | 500 | 0 | |
| HF | 249 | 249 | 0 | |
| 244bb | 600 | 113 | 487 | 81.2 |

-continued

| component | Feed to the system g/hr | OH take-off g/hr | Bottoms take-off g/hr | 244bb recovery % |
|---|---|---|---|---|
| 1233xf | 400 | 400 | 0 | |
| HF | 199 | 199 | 0 | |
| 244bb | 700 | 75 | 625 | 89.3 |
| 1233xf | 300 | 300 | 0 | |
| HF | 146 | 146 | 0 | |
| 244bb | 800 | 56 | 744 | 92.9 |
| 1233xf | 200 | 200 | 0 | |
| HF | 100 | 100 | 0 | |
| 244bb | 900 | 28 | 872 | 96.9 |
| 1233xf | 100 | 100 | 0 | |
| HF | 50 | 50 | 0 | |

We claim:

1. A method for separating HCFC-244bb from a binary azeotropic mixture with HCFO-1233xf comprising:
    adding a hydrogen fluoride to the binary azeotropic mixture such that HCFC-244bb, HCFO-1233xf, and hydrogen fluoride form a ternary azeotropic mixture; and
    distilling the ternary azeotrope from the solution such that a portion of HCFC-244bb remains in solution and substantially all of the HCFO-1233xf is removed.

2. The method of claim 1 wherein approximately 10 to 50 wt % of the binary mixture is comprised of the HCFC-244bb and approximately 50 to 90 wt % of the binary mixture is comprised of HCFO-1233xf.

3. The method of claim 2 wherein approximately 0.1-10 wt % of hydrogen fluoride is added to the binary mixture to form the ternary azeotropic mixture.

4. The method of claim 1 wherein the concentration of HCFC-244b in the ternary azeotrope is between about 10.0-18.0 wt %.

5. The method of claim 1 wherein the concentration of HCFO-1233xf in the ternary azeotrope is between about 51.0-64.0 wt %.

6. The method of claim 1 wherein the concentration of hydrogen fluoride in the ternary azeotrope is between about 23-35 wt %.

7. The method of claim 1 wherein the boiling point of the ternary azeotrope is about 0° C. to about 61° C. at a pressure of about 15 psia to about 108 psia.

8. The method of claim 7 wherein the ternary azeotrope has a boiling point selected from the group consisting of about 23° C. at a pressure of about 37 psia, about 0° C. at a pressure of about 15 psia and about 61° C. at a pressure of about 108 psia.

9. The method of claim 1 wherein a yield of approximately 60 to 97% of HCFC-244b is recovered from the ternary azeotropic mixture.

10. A method for separating HCFC-244bb from a binary azeotropic mixture with HCFO-1233xf comprising:
    providing a binary azeotropic mixture of approximately 10 to 50 wt % HCFC-244bb and approximately 50 to 90 wt % HCFO-1233xf;
    adding approximately 0.1-10 wt % of hydrogen fluoride to the binary azeotropic mixture such that HCFC-244bb, HCFO-1233xf, and hydrogen fluoride form a ternary azeotropic mixture having a boiling point of about 0° C. to about 61° C. at a pressure of about 15 psia to about 108 psia; and
    distilling the ternary azeotrope from the solution such that a portion of HCFC-244bb remains in solution and substantially all of the HCFO-1233xf is removed.

11. The method of claim 10 wherein the ternary azeotrope has a boiling point selected from the group consisting of about 23° C. at a pressure of about 37 psia, about 0° C. at a pressure of about 15 psia and about 61° C. at a pressure of about 108 psia.

* * * * *